(12) United States Patent
Ogawa

(10) Patent No.: US 6,923,066 B2
(45) Date of Patent: Aug. 2, 2005

(54) ULTRASONIC TRANSMITTING AND RECEIVING APPARATUS

(75) Inventor: Eiji Ogawa, Kaisei-machi (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 12 days.

(21) Appl. No.: 10/649,681

(22) Filed: Aug. 28, 2003

(65) Prior Publication Data
US 2004/0066708 A1 Apr. 8, 2004

(30) Foreign Application Priority Data
Aug. 30, 2002 (JP) .................................. 2002-252398

(51) Int. Cl.$^7$ .............................................. G01N 29/10
(52) U.S. Cl. .......................................... 73/626; 600/447
(58) Field of Search .................... 73/625, 626; 600/447

(56) References Cited

U.S. PATENT DOCUMENTS

| 5,720,708 A | 2/1998 | Lu et al. |
| 6,066,099 A * | 5/2000 | Thomenius et al. ........ 600/447 |
| 6,179,780 B1 | 1/2001 | Hossack et al. |

FOREIGN PATENT DOCUMENTS

JP 09-299370 11/1997

OTHER PUBLICATIONS

Jian–yu Lu 2D and 3D High Frame Rate Imaging with Limited Diffraction Beams IEEE Transactions of Ultrasonics, Feroelectrics and Frequency Cotnrol, vol. 44, N.o 4, Jul. 1997.

Jian–yu Lu A Study Of Two–Dimensional Array Transducers for Limited Diffraction Beams IEE Transactions of Ultrasonics, Ferroelectrics and Frequency Control, vol. 41, No. 5, Sep. 1994.

* cited by examiner

Primary Examiner—John E. Chapman
(74) Attorney, Agent, or Firm—Sughrue Mion, PLLC (57) ABSTRACT

An ultrasonic transmitting and receiving apparatus capable of scanning an object to be inspected in high density and in a short time by using nondiffracting beams. The ultrasonic transmitting and receiving apparatus includes: an ultrasonic transducer array including ultrasonic transducers arranged in a matrix form; a waveform information setting unit for setting waveform information to be used for transmitting a plurality of ultrasonic beams, each of which is synthesized by ultrasonic signals having amplitude and phase characteristics represented by Bessel function, within a predetermined period; and a drive signal generating unit for respectively generating drive signals for driving the ultrasonic transducers included in the ultrasonic transducer array on the basis of the waveform information set by the waveform information setting unit.

4 Claims, 12 Drawing Sheets

ULTRASONIC TRANSMITTING AND RECEIVING APPARATUS

BACKGROUND OF THE INVENTION

1. Field of the Invention

The present invention relates to an ultrasonic transmitting and receiving apparatus for transmitting ultrasonic waves and receiving echo signals, thereby obtaining ultrasonic images.

2. Description of a Related Art

Conventionally, as an element used for transmitting and receiving ultrasonic waves, that is, an ultrasonic transducer, a piezoelectric element that includes piezoelectric ceramic represented by PZT (Pb (lead) zirconate titanate) or macromolecule piezoelectric material represented by PVDF (polyvinylidene difluoride) has been generally used.

Figure 13:
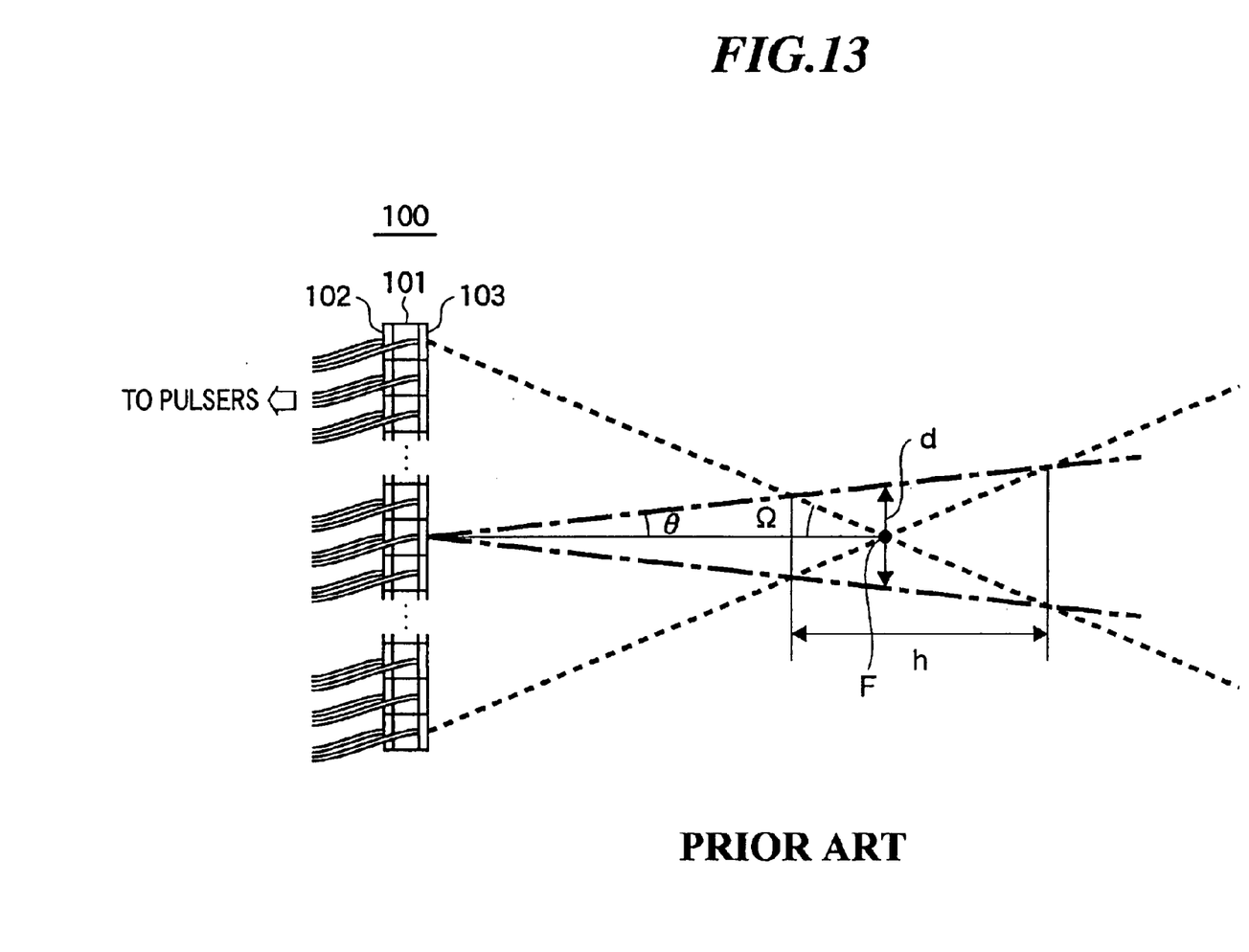
FIG. 13 is a view showing an acoustic distribution of a diffracting beam transmitted from a conventional ultrasonic transducer array.

FIG. 13 shows a structure of a transducer included in an ultrasonic probe that is generally used in an ultrasonic imaging apparatus and an acoustic field distribution of an ultrasonic beam transmitted from the transducer. As shown in FIG. 13, the ultrasonic transducer array 100 is fabricated by, for example, linearly arranging a number of piezoelectric elements 101 on ends of which electrodes 102 and 103 are formed. A drive signal generating circuit including a pulser etc. is connected to the electrodes 102 and 103. Applying a voltage to such piezoelectric elements via the electrodes, the piezoelectric elements expand and contract by a piezoelectric effect to generate ultrasonic waves. By driving plural piezoelectric elements at predetermined time intervals, spherical waves transmitted from the respective piezoelectric elements are synthesized and a focus F of the ultrasonic beam can be formed in a desired direction and a desired depth.

The acoustic field of the ultrasonic wave formed as described above can be defined by an angle $\Omega$ in anticipation of the focal position from an aperture of the ultrasonic transducer array 100 and a directivity angle $\theta$ determined by an aperture of a transducer. That is, as shown in FIG. 13, the ultrasonic wave transmitted from the ultrasonic transducer array 100 converges once around the focus F and is diffused again. Further, in front and back of the focus F, a narrow beam zone "h" is shown.

By the way, in order to improve image quality of an ultrasonic image, it is necessary to improve resolving power when transmitting and receiving the ultrasonic beams. Under present circumstances, axial resolving power depending on ultrasonic frequency is sufficient, but lateral resolving power depending on beam width (beam diameter) is not yet sufficient. To improve the lateral resolving power, the beam is required to be narrowed. However, as clearly understood from FIG. 13, the narrow beam zone is short in the conventional beam focusing technique, and therefore, a zone in which the lateral resolving power is good is small. Furthermore, in the ultrasonic beam formed by the synthesis of spherical waves as described above, there occurred a problem that energy efficiency of the beam is very bad in the vicinity of the focus.

As a countermeasure against such problems, it is proposed to use a nondiffracting beam. The nondiffracting beam means a beam having an unchangeable section pattern regardless of the distance. As the nondiffracting beam, an X-wave (see U.S. Pat. No. 5,720,708) and a Bessel beam are known. The Bessel beam is an ultrasonic beam to be transmitted in distribution, amplitude, and phase expressed by Bessel function. The theory of the Bessel beam is held in an infinite aperture, however, it is shown that the nondiffracting depth can be ensured in a finite aperture to some degree (see J. Durnin, "Exact solutions for nondiffracting beams. I. The scalar theory", J. Opt. Soc. Am. 1987, Vol. 4, No. 4, pp.651–654). Note that the nondiffracting depth means a depth that the nondiffracting beam can reach within medium without changing its waveform.

The nondiffracting beam propagates to the nondiffracting depth without diffusing energy. Therefore, in the case where the beam can be applied to the ultrasonic transmission and reception, a zone of a uniform beam width is maintained, and therefore, ultrasonic imaging can be performed in which improvements of the lateral resolving power, the energy efficiency and so on are realized. For example, in the Japanese Unexamined Patent Application Publication JP-A-9-299370, an ultrasonic probe for transmitting ultrasonic waves according to Bessel function is disclosed. In JP-A-9-299370, there is described that, by using a Bessel beam, a structure of an electric circuit can be made relatively simple, images with high resolution power and good quality can be obtained, and request for decrease in diameter can be accommodated. Alternatively, obtaining a two-dimensional or three-dimensional image by transmitting and receiving the nondiffracting beam (see Jian-yu Lu, "2D and 3D High Frame Rate Imaging with Limited Diffraction Beams", IEEE TRANSACTIONS ON ULTRASONICS, FERROELECTRICS, AND FREQUENCY CONTROL, Vol. 44, No. 4, JULY 1997, pp.839–856) and steering of the nondiffracting beam (see Jian-yu Lu, "A Study of Two-Dimensional Array Transducers for Limited Diffraction Beams", IEEE TRANSACTIONS ON ULTRASONICS, FERROELECTRICS, AND FREQUENCY CONTROL, Vol. 41, No. 5, SEPTEMBER 1994, pp.724–739) are also described.

On the other hand, conventionally, in order to obtain a two-dimensional or three-dimensional image, for example, like B-mode scanning, an ultrasonic beam is transmitted one by one to scan an object to be inspected, and a two-dimensional or three-dimensional image is synthesized on the basis of the obtained image information. However, according to such method, time lag between frames is large, and therefore, images in different times will be synthesized. On this account, when imaging moving regions, the synthesized image is blurred. Especially, when observing a region moving hard such as a circulatory organ, real time environment of at least 30 frames per second is required.

As a countermeasure against such problems, a simultaneous multidirectional transmission and reception technique is under study (see U.S. Pat. No. 6,179,780 B1). However, since the beam focusing technique disclosed in U.S. Pat. No. 6,179,780 B1 uses conventional phase matching, the problem between the resolving power of the ultrasonic beam and the length of the narrow beam zone and the problem of the energy efficiency in the focus still remain.

SUMMARY OF THE INVENTION

The present invention has been achieved in view of the above-described problems. An object of the present invention is to provide an ultrasonic transmitting and receiving apparatus capable of scanning an object to be inspected with high resolution power and high efficiency in a short time by using nondiffracting beams.

In order to solve the above-described problems, an ultrasonic transmitting and receiving apparatus according to the present invention comprises: an ultrasonic transducer array including a plurality of ultrasonic transducers arranged in a matrix form; waveform information setting means for setting waveform information to be used for transmitting a plurality of ultrasonic beams, each of which is synthesized by a plurality of ultrasonic signals having amplitude and phase characteristics represented by Bessel function, within a predetermined period; and drive signal generating means for generating a plurality of drive signals for driving the plurality of ultrasonic transducers included in the ultrasonic transducer array, respectively, on the basis of the waveform information set by the waveform information setting means.

According to the present invention, since multi-beam transmission is performed by using the Bessel beam as a kind of nondiffracting beam, it is possible to scan an object to be inspected with high resolution power and high efficiency in a short time.

DESCRIPTION OF THE PREFERRED EMBODIMENTS

Hereinafter, embodiments of the present invention will be described in detail by referring to the drawings. The same component elements will be given with the same reference numerals and the descriptions thereof will be omitted.

Figure 1:
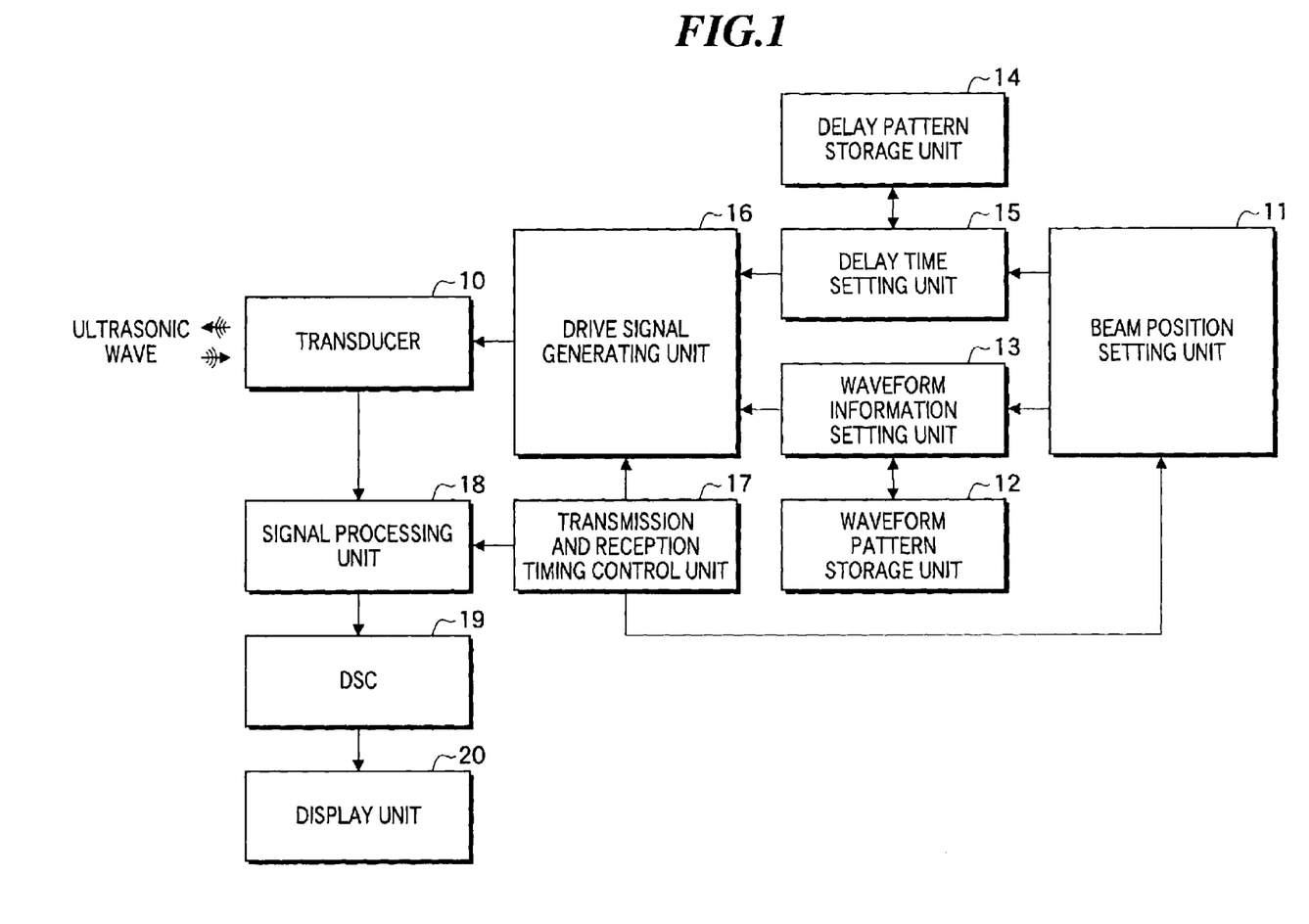
FIG. 1 is a block diagram showing a constitution of an ultrasonic transmitting and receiving apparatus according to a first embodiment of the present invention.

FIG. 1 is a block diagram showing an ultrasonic transmitting and receiving apparatus according to a first embodiment of the present invention. The ultrasonic transmitting and receiving apparatus according to this embodiment is for obtaining information on an object to be inspected by transmitting a plurality of Bessel beams, which belong to a kind of diffracting beam, as ultrasonic beams from different areas simultaneously or almost simultaneously. Hereinafter, simultaneous or almost simultaneous transmission of plural ultrasonic beams is referred to as multi-beam transmission.

First, a Bessel beam transmitted in this embodiment will be described. The Bessel beam is a kind of nondiffracting beam and it means an ultrasonic beam represented by Bessel function expressed by the following equation in this application.

$$Y = J_0(\alpha X) \quad (1)$$

In Eq. (1), $J_0$ is a sign representing Bessel function of the order 0, and $\alpha$ is an arbitrary constant number.

Figure 2A:
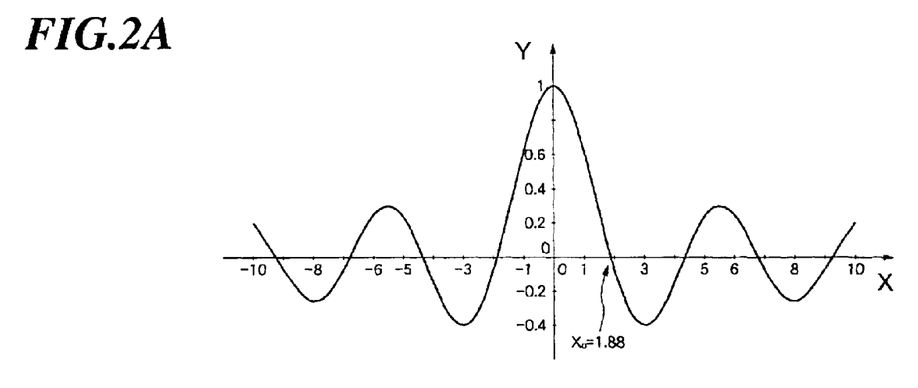
FIG. 2A is a graph showing Bessel function.

FIG. 2A is a graph representing Eq. (1). In the case where this function is applied to transmission of ultrasonic waves, X corresponds to a distance from the array center of the ultrasonic transducers that generate ultrasonic waves, and Y corresponds to intensity (amplitude) of the ultrasonic waves. As shown in FIG. 2A, a main beam having high intensity exists in the vicinity where X=0, in the zero order Bessel function.

The beam radius of the main beam is expressed by $X=X_0$ where Bessel function $J_0(\alpha X)=0$. Here, since the solution to the zero order Bessel function $J_0(\alpha X)$ is given as $\alpha X_0 = 0.766\pi$, the main beam having an arbitrary beam width can be formed by setting the constant number $\alpha$. The value $X_0$ is referred to as "zero cross radius".

Note that, practically, even in the case where the Bessel beam is transmitted from a finite aperture, a certain degree of nondiffracting depth can be ensured. The following equation (2) is an equation for obtaining the nondiffracting depth in the case where the Bessel beam is transmitted from the finite aperture.

$$Z_{MAX} = r \times \sqrt{\left(\frac{2\pi}{\alpha\lambda}\right)^2 - 1} \quad (2)$$

In Eq. (2), "r" represents a radius of the aperture, and $\lambda$ represents a wavelength of an ultrasonic wave. As clearly understood from Eq. (2), when the radius of the aperture is enlarged, the nondiffracting depth $Z_{Max}$ becomes longer. However, in practice, since the size of the probe used for the object such as a human body is restricted, it is difficult to enlarge the radius of the aperture. Further, according to Eq. (2), it is known that the shorter the wavelength $\lambda$ is, the longer the nondiffracting depth $Z_{MAX}$ becomes, and therefore, the frequency of an ultrasonic wave may be made higher for this purpose. However, an ultrasonic wave becomes easier to be absorbed by medium when the frequency is made higher, and as a result, sufficient intensity of an ultrasonic wave cannot be obtained in a deep part of the object.

On this account, in order to elongate the nondiffracting depth $Z_{MAX}$ of the Bessel beam, it is desired that the zero cross radius $X_0$, i.e., the main beam radius is enlarged so as to make the value of the constant number a small. Here, enlarging the main beam width results in reducing the lateral resolution power. Therefore, it is important to determine the main beam width in relation to the nondiffracting depth within a range not exerting an influence on image quality.

Figure 3:
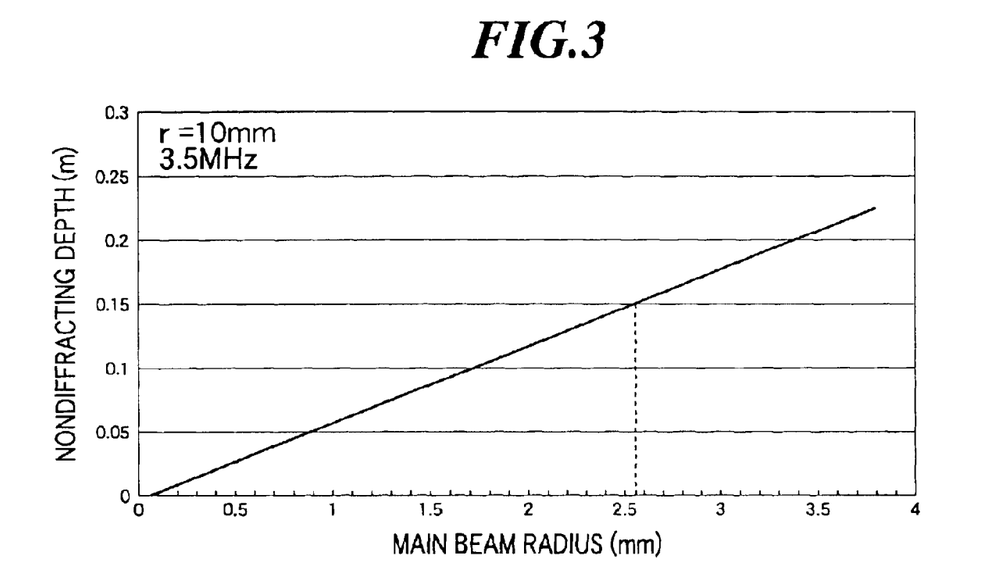
FIG. 3 is a view showing relationship between a main beam radius of a Bessel beam and a nondiffracting depth.

FIG. 3 is a graph representing the relationship between the main beam radius and the nondiffracting depth, which is made in accordance with Eq. (2). Here, it is assumed that the radius (r) of the aperture is 10 mm, the frequency is 3.5 MHz, an acoustic velocity is 1540 m/s, and the wavelength ($\lambda$) of an ultrasonic wave is $4.4\times10^{-4}$ m. For example, when observing a heart of a human body, the nondiffracting depth of about 0.15 m may be sufficient. According to FIG. 3, the sufficient nondiffracting depth can be obtained by making the main beam radius about 2.5 mm. Since this main beam radius is smaller than a beam radius of a diffracting beam used in a general ultrasonic transmitting and receiving apparatus, higher lateral resolving power than that in such apparatus can be obtained.

Next, a method of realizing the Bessel beam will be described. When determining Bessel function, at first, the main beam radius $X_0$ is specified while paying attention to the points described above. Thereby, the value of the constant number $\alpha$ is determined from the solution to the zero order Bessel function, that is, $\alpha X_0 = 0.766\pi$. Note that FIG. 2A is a graph in the case where the zero cross radius is assumed as $X_0 = 1.88$ mm, i.e., $\alpha = 1.28$ mm$^{-1}$.

When forming an ultrasonic beam on the basis of the Bessel function determined as described above, coordinates of Bessel function and ultrasonic transducers arranged in a matrix form are correlated, and the ultrasonic transducer located in the coordinate X is driven by a waveform having amplitude $Y = J_0(\alpha X)$. Concurrently, the transducers located in an area where $Y<0$ in Bessel function are driven by a waveform having an inversed phase.

Figure 2B:
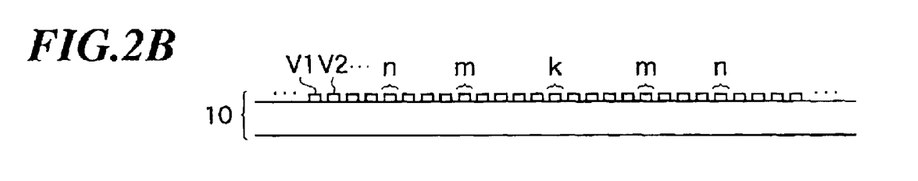
FIGS. 2B and 2C are views for explanation of a method of transmitting an ultrasonic beam expressed by the Bessel function.
Figure 2C:
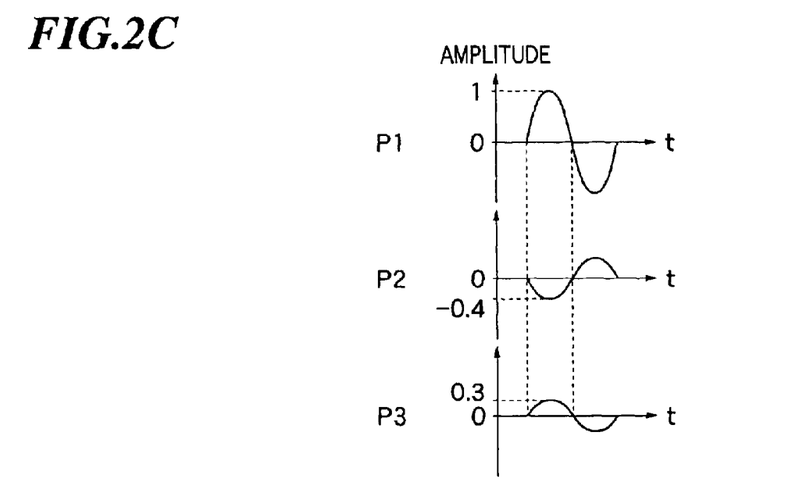

FIG. 2B shows ultrasonic transducers V1, V2, . . . used when transmitting the ultrasonic beam represented by Bessel function shown in FIG. 2A. Further, FIG. 2C shows waveform information P1, P2, . . . used for driving the respective ultrasonic transducers. For example, the ultrasonic transducer located in the vicinity of the central position of the Bessel beam (area "k") is driven on the basis of the waveform information P1 having amplitude $Y=1$. Further, the ultrasonic transducer in the vicinity of an area "m" outside of the area "k" is driven on the basis of the waveform information P2 having amplitude $Y=0.4$ and an inversed phase relative to that in the area "k". Furthermore, the transducer in the vicinity of an area "n" outside of the area "m" is driven on the basis of the waveform information P3 having amplitude $Y=0.3$ and the same phase as that in the area "k". Thus, the matrix array transducer is driven in relation to the distribution of the Bessel function. By synthesizing the ultrasonic waves transmitted from these ultrasonic transducers, the Bessel beam as shown in FIG. 2A is formed. Here, the ultrasonic transducers are arranged in a two-dimensional manner, and, the Bessel beam extended in three dimensions is transmitted by driving these ultrasonic transducers in equal directions and in accordance with distances from the center of Bessel function. By the way, in the case where the ultrasonic transducers are arranged in one-dimensional manner, the ultrasonic beam having diffraction characteristics with respect to one direction can be formed.

Referring to FIG. 1 again, the ultrasonic transmitting and receiving apparatus according to this embodiment will be described in detail. This ultrasonic transmitting and receiving apparatus has a matrix array transducer 10, a beam position setting unit 11, a waveform pattern storage unit 12, a waveform information setting unit 13, a delay pattern storage unit 14, a delay time setting unit 15, a drive signal generating unit 16, a transmission and reception timing control unit 17, a signal processing unit 18, a digital scan converter (DSC) 19, and a display unit 20.

The matrix array transducer 10 includes a plurality of ultrasonic transducers arranged in a matrix form and has an aperture area of about 20 mm square, for example. The matrix array transducer 10 transmits an ultrasonic beam on the basis of an applied drive signal, and receives a propagating ultrasonic wave and outputs a detection signal. These ultrasonic transducers are constituted by vibrators in which electrodes are formed on ends of piezoelectric elements that include material having a piezoelectric property such as piezoelectric ceramic represented by PZT (Pb (lead) zirconate titanate) or macromolecule piezoelectric material represented by PVDF (polyvinylidene difluoride). Applying a voltage to the electrodes of such vibrators by transmitting a pulse form electric signal or a continuous wave electric signal, the piezoelectric elements expand and contract by a piezoelectric effect. Thereby, ultrasonic pulses or continuous ultrasonic waves are generated from the respective vibrators and an ultrasonic beam is formed by synthesizing these ultrasonic waves. In addition, the respective vibrators expand and contract by receiving propagating ultrasonic waves, and generate electric signals. These electric signals are outputted as detection signals of the ultrasonic waves.

Alternatively, as the ultrasonic transducer, plural kinds of elements using different ultrasonic conversion methods may be used. For example, the above-described vibrator is used as an element for transmitting ultrasonic waves, and a photo-detection type ultrasonic transducer is used as an element for receiving ultrasonic waves. The photo-detection type transducer is for detecting an ultrasonic signal by converting it into an optical signal, and it can be constituted by a Fabry-Perot resonator or a fiber Bragg grating, for example.

Figure 4:
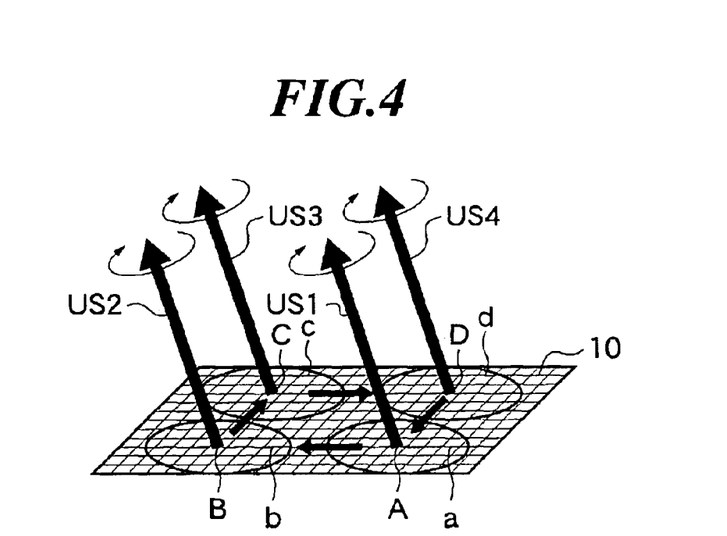
FIG. 4 is a view showing Bessel beams subjected to multi-beam transmission from a plurality of sub-arrays, central positions thereof.

Here, in this embodiment, for the purpose of performing multi-beam transmission of Bessel beams, Bessel beams are transmitted from plural areas, respectively, by dividing the ultrasonic transmission surface of the matrix array transducer 10 into plural areas and treating the respective areas as single apertures. Hereinafter,the sets of the plural ultrasonic transducers included in these divided areas are referred to as sub-arrays. As shown in FIG. 4, for example, plural ultrasonic transducers included in sub-array "a" are used for transmitting ultrasonic beam US1. Similarly, ultrasonic beam s US2 to US4 are transmitted by using ultrasonic transducers included in sub-arrays "b" to "d", respectively.

The beam position setting unit 11 sets positions that become centers of the Bessel beams in the coordinates on the matrix array transducer 10. Because, when forming the Bessel beam in this embodiment, the waveform information for driving the respective ultrasonic transducers is set with reference to the central position of the Bessel beam. FIG. 4 shows central positions A to D of the ultrasonic waves US1 to US4, respectively.

The waveform pattern storage unit 12 stores waveform information, which includes amplitude and phase characteristics and is provided to the respective transducers, as waveform patterns corresponding to the positions of ultrasonic transducers. That is, for example, the storage unit stores the wave information P1, P2, . . . as shown in FIG. 2C.

The waveform information setting unit 13 sets wave information to be used for driving a predetermined ultrasonic transducers, on the basis of the central position set by the beam position setting unit 11 and the waveform pattern stored in the waveform pattern storage unit 12. That is, the waveform information setting unit 13 correlates the above-described waveform patterns with the ultrasonic transducers arranged in a matrix with reference to the plural central positions set by the beam position setting unit 11. For example, by correlating the waveform patterns shown in FIG. 2C with the matrix array transducer with each of the positions A to D shown in FIG. 4 as a center, four sub-arrays "a" to "d" having diameters of about 10 mm are set. The setting is performed so that the waveform information P1, P2, . . . shown in FIG. 2C may be provided to the plural ultrasonic transducers included in each of the sub-arrays "a" to "d".

The delay pattern storage unit 14 stores plural delay patterns to be used when steering the ultrasonic beam.

The delay time setting unit 15 selects a suitable pattern from the plural delay patterns stored in the delay pattern storage unit 14 in order to steer the Bessel beam in a desired direction. Further, the delay time setting unit 15 sets delay times corresponding to the respective ultrasonic transducers by correlating the central positions set by the beam position setting unit 11 and the selected delay pattern.

Figure 5A:
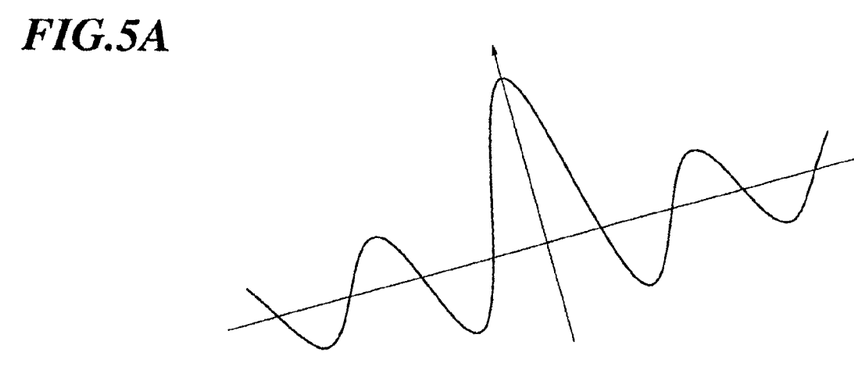
FIGS. 5A to 5C are views for explanation of a method of steering the Bessel beam.
Figure 5B:
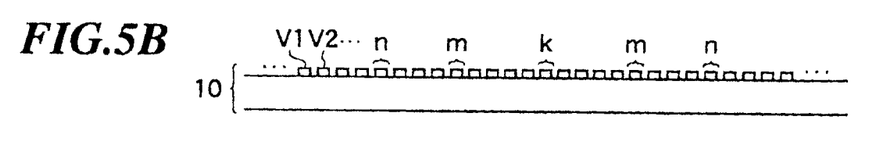
Figure 5C:
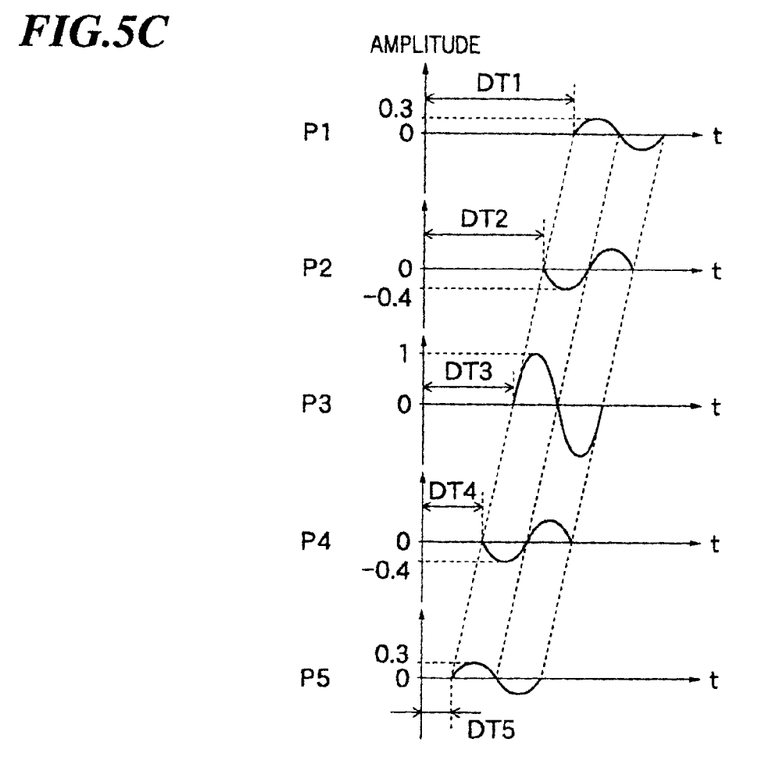

The drive signal generating unit 16 is constituted by, for example, plural pulsers respectively corresponding to the plural ultrasonic transducers included in the matrix array transducer 10. Here, referring to FIGS. 5A to 5C, the drive signal generating unit 16 generates plural drive signals toward the plural ultrasonic transducers V1, V2, . . . included in the matrix array transducer 10 as shown in FIG. 5B, on the basis of the waveform information P1, P2, . . . set in the waveform information setting unit 13 and delay times DT1, DT2, . . . set in the delay time setting unit 15 as shown in FIG. 5C, respectively. Thereby, ultrasonic waves having predetermined amplitude and phase are generated at predetermined times from the plural ultrasonic transducers V1, V2, . . . , respectively, and the Bessel beam steered in a direction of an arrow as shown in FIG. 5A is transmitted.

The transmission and reception timing control unit 17 controls the drive signal generating unit 16 to generate drive signals at predetermined timings, and controls the signal processing unit 18 to capture the detection signals outputted from the matrix array transducer 10 after a fixed period of time has elapsed from the transmission times of the ultrasonic waves. Thus, by limiting the time periods for reading the signals by controlling the drive signals and the detection signals, echo signals reflected from a specific depth in the object can be detected.

The signal processing unit 18 captures detection signals that the plural ultrasonic transducers included in the matrix array transducer 10 outputs by receiving the ultrasonic waves at predetermined timings according to the control of the transmission and reception timing control unit 17. The signal processing unit 18 performs gain adjustment to these signals and reception focusing by performing addition with predetermined delays. By this reception focusing, the focus of the received ultrasonic signal can be narrowed. At that time, the reception focusing may be performed by generally performed delay addition, or by weighting addition on the basis of the waveform patterns used when transmitting the Bessel beams. The latter case is more desirable because the beam width of the received beam can be set narrower and the zone where the beam width is narrow can be set longer than in the former case. Further, the signal processing unit 18 performs signal processing such as logarithmic amplification, demodulation, STC (sensitivity time control), and A/D conversion on the detection signals subjected to reception focusing.

The DSC 19 performs scan-converting on the detection signals subjected to signal processing in the signal processing unit 18. In addition, the display unit 20 is, for example, a display device such as a CRT or an LCD, and displays an ultrasonic image based on the signals subjected to the scan-converting by the DSC 19.

In the above-described ultrasonic transmitting and receiving apparatus, by performing the multi-beam transmission in a number of times while changing the steering direction, the object can be scanned with high-density. At that time, the density of scanning of the object can be made even higher by performing the above-described scanning while shifting the transmission positions of the Bessel beams by changing the central positions in the beam position setting unit 11.

Figure 6:
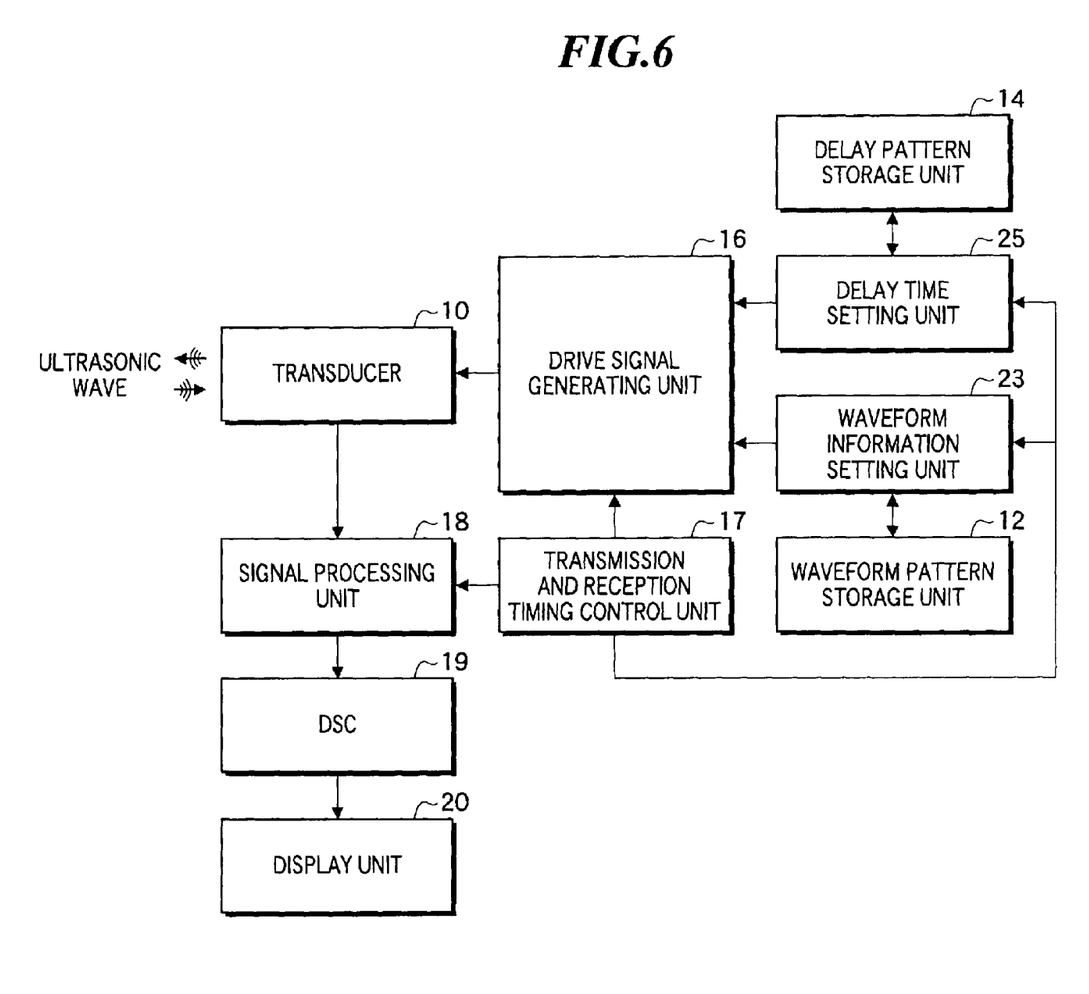
FIG. 6 is a block diagram showing a constitution of an ultrasonic transmitting and receiving apparatus according to a second embodiment of the present invention.

Next, an ultrasonic transmitting and receiving apparatus according to a second embodiment of the present invention will be described by referring to FIGS. 6 to 8. FIG. 6 is a block diagram showing a constitution of the transmitting and receiving apparatus according to this embodiment.

The ultrasonic transmitting and receiving apparatus according to this embodiment has a waveform information setting unit 23 and a delay time setting unit 25 instead of the waveform information setting unit 13 and the delay time setting unit 15 in the ultrasonic transmitting and receiving apparatus shown in FIG. 1. Further, this ultrasonic transmitting and receiving apparatus does not have the beam position setting unit 11 in the ultrasonic transmitting and receiving apparatus shown in FIG. 1. The constitution other than the above is the same as that described in the first embodiment.

Figure 7:
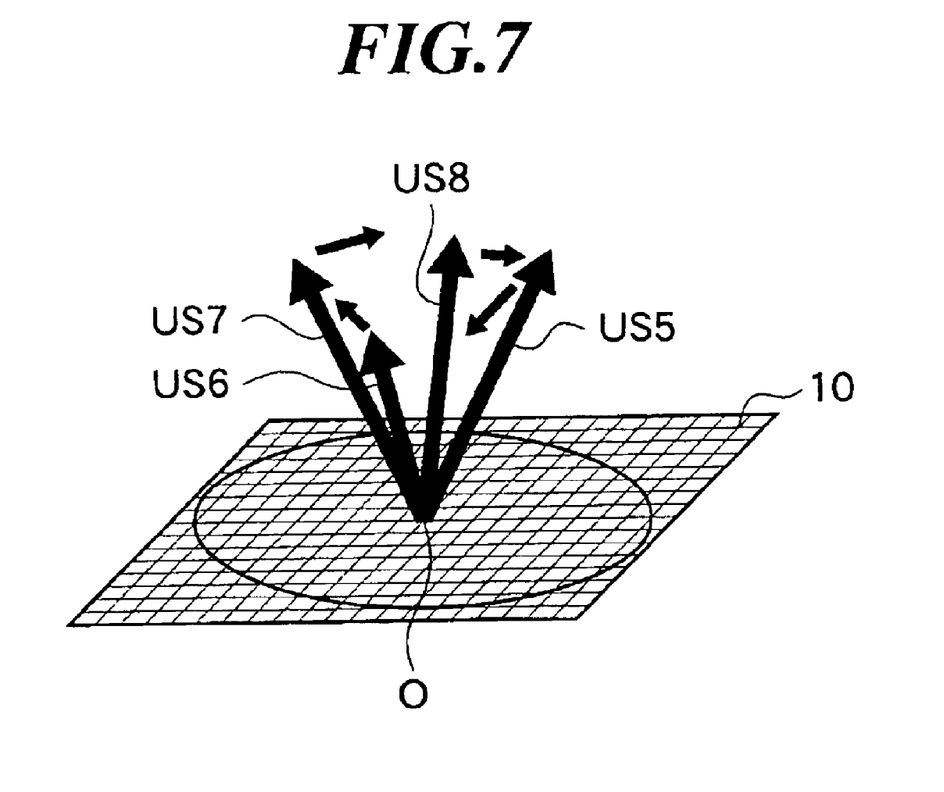
FIG. 7 is a view showing Bessel beams subjected to multi-beam transmission from one sub-array while being steered.

As shown in FIG. 7, the ultrasonic transmitting and receiving apparatus according to this embodiment is for transmitting plural Bessel beams US5 to US8 from the same position. In this embodiment, a central position O from which the Bessel beams are transmitted is preset at the center of the matrix array transducer 10.

The waveform information setting unit 23 sets waveform information to be provided to the respective ultrasonic transducers on the basis of the waveform patterns stored in the waveform pattern storage unit 12. The waveform information to be provided to the respective ultrasonic transducers is determined by correlating the centers of the waveform patterns with the center of the matrix array transducer 10.

The delay time setting unit 25 selects suitable delay patterns for the respective transmitted Bessel beams from the plural delay patterns stored in the delay pattern storage unit 14. Further, the delay time setting unit 25 correlates the centers of the selected delay patterns with the center of the matrix array transducer 10, and sets delay times to be provided to the respective ultrasonic transducers for the respective patterns.

Figure 8A:
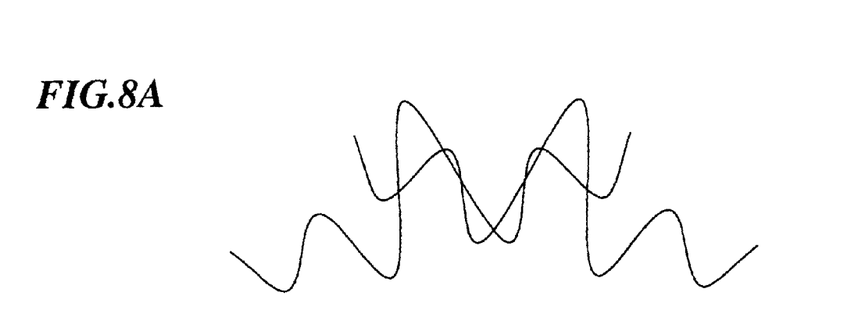
FIGS. 8A to 8C are views for explanation of a method of steering a plurality of Bessel beams subjected to multi-beam transmission.
Figure 8B:
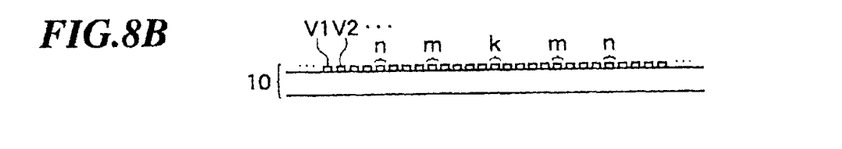
Figure 8C:
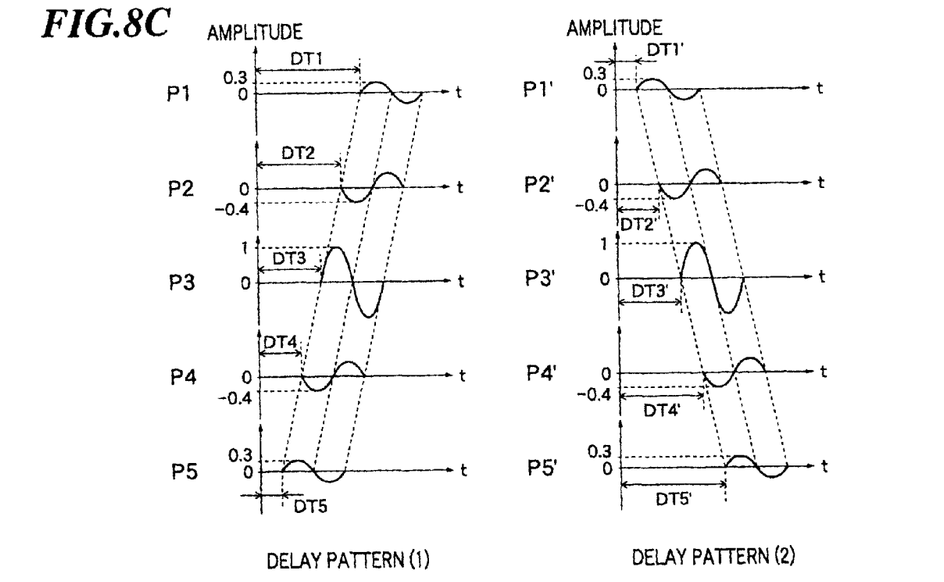

Here, referring to FIGS. 8A to 8C, waveform information P1, P2 ... P5 and waveform information P1', P2' ... P5' as shown in FIG. 8C are provided to the plural ultrasonic transducers V1, V2, ... as shown in FIG. 8B in accordance with distances from the center of the matrix array transducer 10 and steering angles. As shown in FIG. 8A, in order to simultaneously transmit the Bessel beams steered in different directions, these pieces of waveform information prepared for the steering angles may be added. For example, the ultrasonic transducer in the vicinity of an area "n" is first driven on the basis of the waveform information P1' after a delay time DT1' is elapsed from the reference time (t=0), and then, driven on the basis of the waveform information P1 after a delay time DT1 is elapsed from the reference time. The ultrasonic transducers in other areas are similarly driven. Here, in the case where two pieces of wave information having a common delay time are set in one ultrasonic transducer from among pieces of the waveform information included in the two delay patterns (1) and (2) as shown in FIG. 8C, these waveforms are added to each other. For example, in the case where the delay time DT3 of the waveform information P3 and the delay time DT3' of the waveform information P3', which are set for the ultrasonic transducer in the vicinity of the area "k", are the same, the amplitude made by synthesizing the waveform information P3 and P3' is provided. Although the case where two Bessel beams are simultaneously transmitted has been explained by referring to FIGS. 8A to 8C, the case where three or more Bessel beams are simultaneously transmitted is similar to that.

In the above-described ultrasonic transmitting and receiving apparatus, by repeating multi-beam transmission while changing steering directions of respective Bessel beams, the high-density scanning within the object can be performed.

Figure 9:
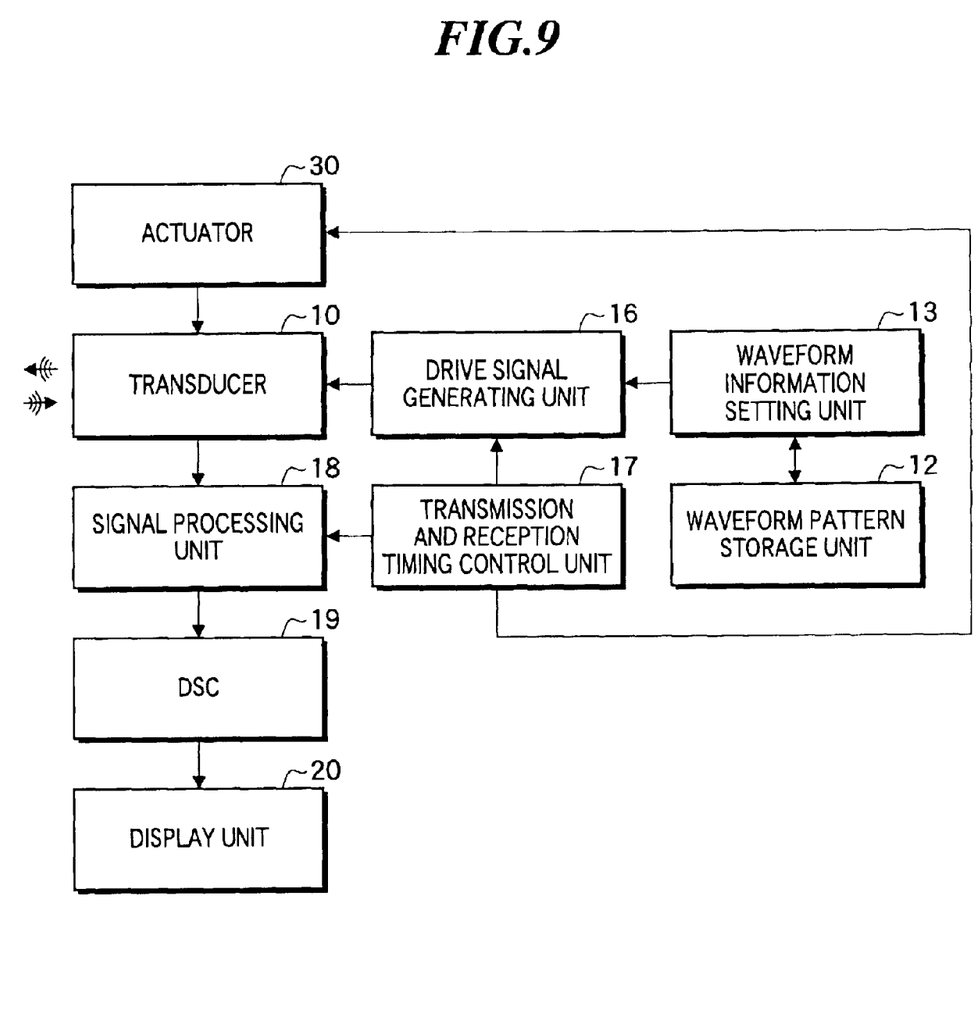
FIG. 9 is a block diagram showing a constitution of an ultrasonic transmitting and receiving apparatus according to a third embodiment of the present invention.

Next, an ultrasonic transmitting and receiving apparatus according to a third embodiment of the present invention will be described by referring to FIGS. 9 and 10. As shown in FIG. 9, the ultrasonic transmitting and receiving apparatus according to this embodiment has an actuator 30 instead of the beam position setting unit 11, the delay pattern storage unit 14, and the delay time setting unit 15 in the ultrasonic transmitting and receiving apparatus shown in FIG. 1. The constitution other than the above is the same as that described in the first embodiment.

Figure 10:
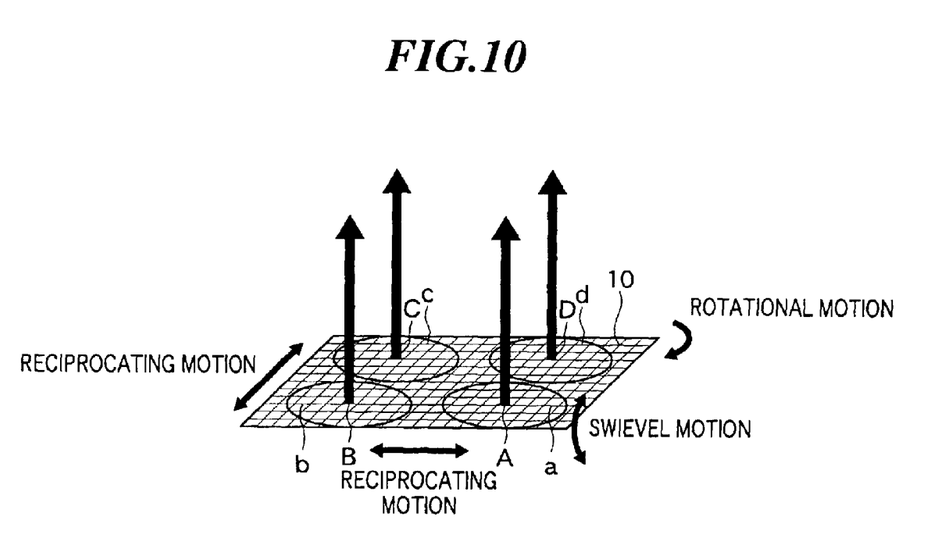
FIGS. 10 is a view showing Bessel beams subjected to multi-beam transmission from a plurality of sub-arrays.

As shown in FIG. 10, in this embodiment, plural central positions A to D and plural sub-arrays "a" to "d" for transmitting the Bessel beams are preset in the matrix array transducer 10. The waveform information setting unit 13 sets waveform information for performing multi-beam transmission by correlating wave form patterns with the fixed plural central positions.

Further, the actuator 30 controls the position of the matrix array transducer 10 and the orientation of the aperture thereof. That is, under the control by the actuator 30, the matrix array transducer 10 performs reciprocating motion, rotational motion, swivel motion and so on.

As described above, by combining the multi-beam transmission for transmitting Bessel beams from the plural positions and mechanical control of the transducers, the plural Bessel beams can be transmitted simultaneously or almost simultaneously while steering the plural Bessel beams. Here, in this embodiment, making the form of the matrix array transducer 10 a convex form, the angles between the plural Bessel beams are enlarged, thereby the scanning within the object can be performed over a wide range.

Figure 11:
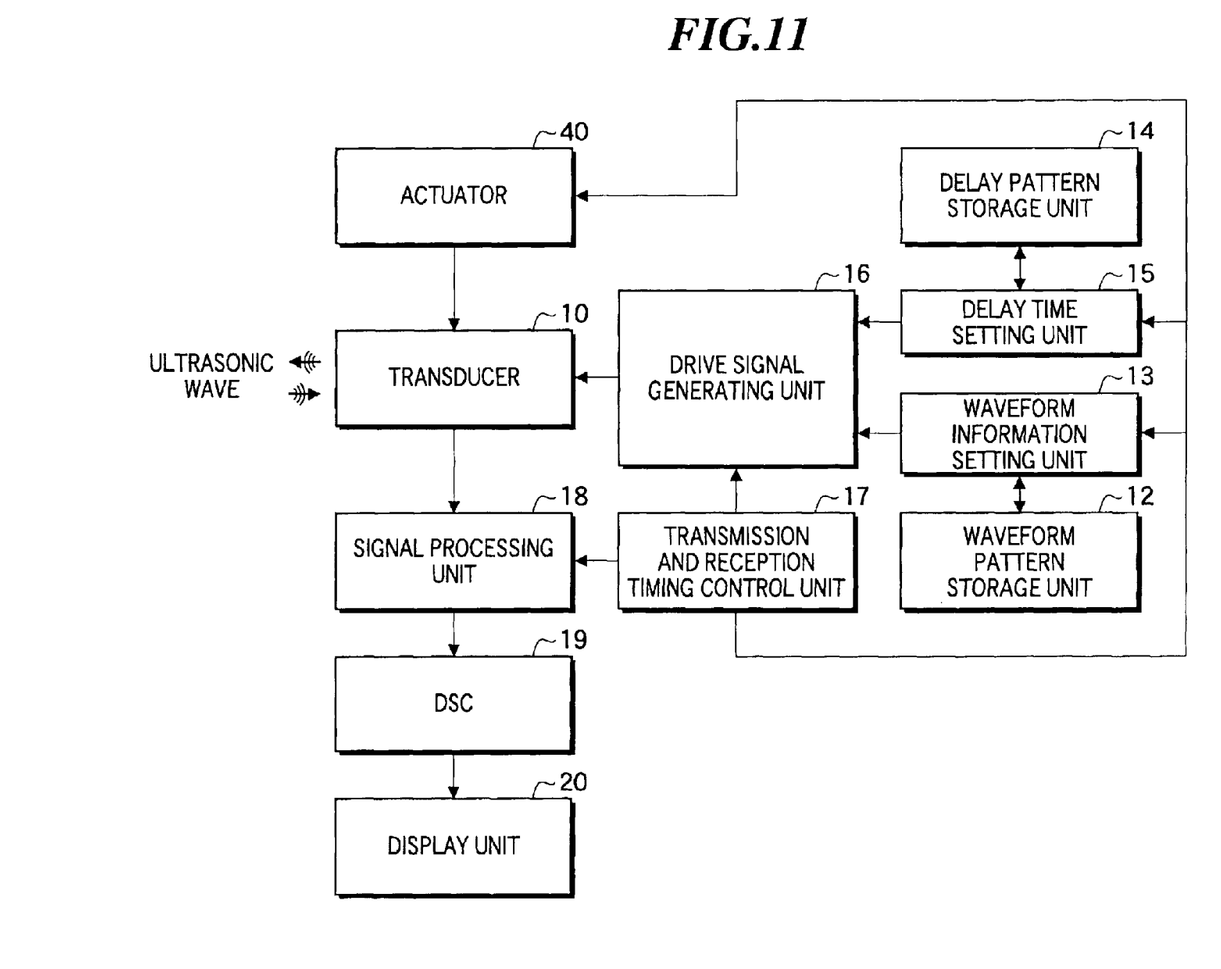
FIG. 11 is a block diagram showing a constitution of an ultrasonic transmitting and receiving apparatus according to a fourth embodiment of the present invention.

Next, an ultrasonic transmitting and receiving apparatus according to a fourth embodiment of the present invention will be described by referring to FIGS. 11 and 12. The ultrasonic transmitting and receiving apparatus according to this embodiment further has an actuator 40 in addition to the ultrasonic transmitting and receiving apparatus shown in FIG. 6. The constitution other than the above is the same as that described in the second embodiment of the present invention.

Figure 12:
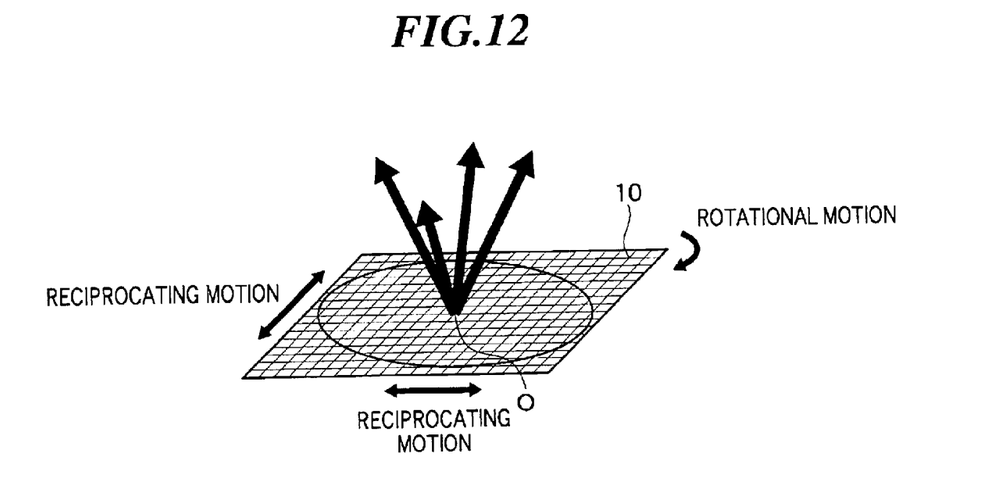
FIG. 12 is a view showing Bessel beams subjected to multi-beam transmission from one sub-array.

As shown in FIG. 12, in this embodiment, a central position O from which the Bessel beams are transmitted is preset at the center of the matrix array transducer 10. From this central position O, plural Bessel beams are transmitted in different directions simultaneously or almost simultaneously.

Further, the actuator 40 controls the position of the matrix array transducer 10 and the orientation of the aperture thereof. That is, under the control by the actuator 40, the matrix array transducer 10 performs reciprocating motion, rotational motion and so on.

As described above, by combining the multi-beam transmission for transmitting Bessel beams from the same position and mechanical control of the transducers, the plural Bessel beams can be transmitted simultaneously or almost simultaneously while steering the plural Bessel beams. Here, also in this embodiment, making the form of the matrix array transducer 10 a convex form, the angles between the plural Bessel beams are enlarged, thereby the wide range scanning angle can be ensured.

According to the present invention, since a Bessel beam is used as a transmitted ultrasonic beam, a narrow beam zone can be made longer, and high resolution power can be obtained over a wide range in depth direction. Further, since energy is not so much diffused in the Bessel beam, the transmission power of the ultrasonic wave can be reduced and intensity of the main beam can be increased by using the same transmission power, thereby ultrasonic imaging with good energy efficiency can be performed.

Furthermore, since the Bessel beam is subjected to multi-beam transmission, the density of the ultrasonic beam scanning within the object at a time can be made higher, and the scanning can be performed within the object over a wide range. Therefore, the frame rate can be improved by shortening the time for ultrasonic imaging, and a two-dimensional or three-dimensional ultrasonic image with high image quality can be obtained in real time.

What is claimed is:

1. An ultrasonic transmitting and receiving apparatus comprising:

an ultrasonic transducer array including a plurality of ultrasonic transducers arranged in a matrix form;

waveform information setting means for setting waveform information to be used for transmitting a plurality of ultrasonic beams substantially simultaneously, each of which is synthesized by a plurality of ultrasonic signals having amplitude and phase characteristics represented by Bessel function; and drive signal generating means for generating a plurality of drive signals for respectively driving said plurality of ultrasonic transducers included in said ultrasonic transducer array on the basis of the waveform information set by said waveform information setting means, wherein said waveform information setting means sets said waveform information so that said plurality of ultrasonic beams are transmitted from different areas included in said ultrasonic transducer array, respectively.

2. The ultrasonic transmitting and receiving apparatus according to claim 1, further comprising:

delay time setting means for setting delay time of the ultrasonic signals in said drive signal generating means so that said plurality of ultrasonic beams are steered; and image generating means for generating an ultrasonic image on the basis of detection signals obtained by receiving ultrasonic echoes.

3. The ultrasonic transmitting and receiving apparatus according to claim 1, further comprising:

control means for controlling at least one of a position of said ultrasonic transducer array and an orientation of an aperture thereof; and image generating means for generating an ultrasonic image on the basis of detection signals obtained by receiving ultrasonic echoes.

4. An ultrasonic transmitting and receiving apparatus comprising:

an ultrasonic transducer array including plurality of ultrasonic transducers arranged in a matrix form;

waveform information setting means for setting waveform information to be used for transmitting a plurality of ultrasonic beams substantially simultaneously, each of which is synthesized by a plurality of ultrasonic signals having amplitude and phase characteristics represented by Bessel function;

drive signal generating means for generating a plurality of drive signals for respectively driving said plurality of ultrasonic transducers included in said ultrasonic transducer array on the basis of the waveform information set by said waveform information setting means;

control means for controlling at least one of a position of said ultrasonic transducer array and an orientation of an aperture thereof; and image generating means for generating an ultrasonic image on the basis of detection signals obtained by receiving ultrasonic echoes, wherein said waveform information setting means sets said waveform information so that said plurality of ultrasonic beams are transmitted from the same area included in said ultrasonic transducer array.

* * * * *